United States Patent [19]

Haak et al.

[11] Patent Number: 5,167,616
[45] Date of Patent: Dec. 1, 1992

[54] IONTOPHORETIC DELIVERY METHOD

[75] Inventors: Ronald P. Haak, San Jose; J. Richard Gyory, Los Altos; Jane Yieh, Millbrae, all of Calif.

[73] Assignee: Alza Corporation, Palo Alto, Calif.

[21] Appl. No.: 452,136

[22] Filed: Dec. 14, 1989

[51] Int. Cl.$^5$ ............................................... A61N 1/30
[52] U.S. Cl. ...................................... 604/20; 128/804
[58] Field of Search .................. 604/20; 128/804, 422, 128/419 R, 632, 647, 604, 128, 734

[56] References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen | 128/207.21 |
| 4,382,529 | 5/1983 | Webster | 604/20 |
| 4,391,278 | 7/1983 | Cahalan et al. | 128/640 |
| 4,398,545 | 8/1983 | Wilson | 128/798 |
| 4,474,570 | 10/1984 | Ariura et al. | 604/20 |
| 4,702,732 | 10/1987 | Powers et al. | 604/20 |
| 4,722,726 | 2/1988 | Sanderson | 604/20 |
| 4,764,164 | 8/1988 | Sasaki | 604/20 |
| 4,767,401 | 8/1988 | Siederman | 604/20 |
| 4,786,277 | 11/1988 | Powers et al. | 604/20 |
| 4,809,707 | 3/1989 | Kraft et al. | 128/736 |
| 4,867,982 | 9/1989 | Campbell et al. | 424/449 |
| 4,878,892 | 11/1989 | Sibalis | 604/20 |
| 4,919,648 | 4/1990 | Sibalis | 604/20 |
| 4,931,046 | 6/1990 | Newman | 604/20 |
| 4,940,456 | 7/1990 | Sibalis | 604/20 |
| 4,942,883 | 7/1990 | Newman | 604/20 |

OTHER PUBLICATIONS

"Spontaneous and Forced Cutaneous Absorption of Indomethacin in Pigs and Humans," Pratzel et al., *The Journal of Rheumatology,* 1986 13:6 pp. 1122–1125.
"Iontophorese zur forcierten Hautresorption von Indometacin und Salicylsäure" Pratzel et al., Ziet Fuer Rheumatology, Nov. 1985, pp. 540–545.
Abramson et al., "Electrophoretic Demonstration of the Patent Pores of the Human Skin, Its Relation to the Charge of the Skin" J. Phys. Chem. vol. 44 pp. 1094–1102 (1940).
Burnette et al., "Comparison Between the Ion and Passive Transport of Thyrotropin Releasing Hormone Across Excised Nude Mouse Skin" J. Pharm. Sci. vol. 75 pp. 738–743 (1986).
Burnette et al., "Characterization of the Pore Transport Properties and Tissue Alteration of Excised Human Skin During Iontophoresis" J. Pharm. Sci. vol. 77 pp. 132–137 (1988).
Bloom et al., "Histogensis of the Skin and Its Accessories" A Textbook of Histology 10th ed. W. B. Saunders, p. 594.
Idson, Bernard "Percutaneous Absorption" Journal of Pharmaceutical Sciences, vol. 64, No. 6, pp. 908–910 (1975).

*Primary Examiner*—Kyle L. Howell
*Assistant Examiner*—Robert L. Nasser, Jr.
*Attorney, Agent, or Firm*—D. Byron Miller; Edward L. Mandell; Steven F. Stone

[57] ABSTRACT

An improved method for delivering a drug or beneficial agent transdermally to humans by iontophoresis is provided. The method includes selecting and iontophoretically delivering the drug through a skin site which optimizes the transdermal delivery rate of the drug while minimizing inter-patient variability in skin resistance.

17 Claims, 2 Drawing Sheets

IONTOPHORETIC DELIVERY METHOD

TECHNICAL FIELD

This invention relates to an improved method for delivering an agent transdermally by iontophoresis. More specifically, this invention relates to a method of increasing the efficiency of an iontophoretic delivery device and to an improved method of using such a device.

BACKGROUND ART

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be transdermally delivered. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, Vernon et al U.S. Pat. No. 3,991,755; Jacobsen et al U.S. Pat. No. 4,141,359; Wilson U.S. Pat. No. 4,398,545; and Jacobsen U.S. Pat. No. 4,250,878 disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be driven into the body is positively charged, then the positive electrode (the anode) will be the active electrode and the negative electrode (the cathode) will serve to complete the circuit. If the ionic substance to be delivered is negatively charged, then the negative electrode will be the active electrode and the positive electrode will be the counter electrode.

Alternatively, both the anode and cathode may be used to deliver drugs of opposite charge into the body. In such a case, both electrodes are considered to be active or donor electrodes. For example, the positive electrode (the anode) can drive a positively charged ionic substance into the body while the negative electrode (the cathode) can drive a negatively charged ionic substance into the body.

It is also known that iontophoretic delivery devices can be used to deliver an uncharged drug or agent into the body. This is accomplished by a process called electroosmosis. Electroosmosis is the volume flow of a liquid (e.g., a liquid containing the uncharged drug or agent) through the skin induced by the presence of an electric field imposed across the skin.

Furthermore, existing iontophoresis devices generally require a reservoir or source of the ionized or ionizable species (or a precursor of such species) which is to be iontophoretically delivered or introduced into the body. Examples of such reservoirs or sources of ionized or ionizable species include a pouch as described in the previously mentioned Jacobsen U.S. Pat. No. 4,250,878, or a pre-formed gel body as disclosed in Webster U.S. Pat. No. 4,382,529. Such drug reservoirs are electrically connected to the anode or the cathode of an iontophoresis device to provide a fixed or renewable source of one or more desired species.

Recently, the transdermal delivery of peptides and proteins, including genetically engineered proteins, by iontophoresis has received increasing attention. Generally speaking, peptides and proteins being considered for transdermal or transmucosal delivery have a molecular weight ranging between about 500 to 40,000 daltons. These high molecular weight substances are too large to passively diffuse through skin at therapeutically effective levels. Since many peptides and proteins carry either a net positive or net negative charge and because of their inability to passively diffuse through skin, they are considered likely candidates for iontophoretic delivery.

In particular, iontophoresis is being considered for long term delivery (i.e., delivery for periods of longer than 24 hours) of a number of drugs, including peptides (e.g., insulin) and proteins. As the length of delivery increases there is a need to develop small unobtrusive iontophoretic delivery devices which can be easily worn on the skin under clothing. One example of a small iontophoretic delivery device designed to be worn on the skin is disclosed in U.S. Pat. 4,474,570. Devices of this type are powered by small low voltage batteries. In addition to the need for developing smaller iontophoretic delivery devices, there is a need to reduce the cost of these devices in order to make them more competitive with conventional forms of therapy such as pills and subcutaneous injections. One method of reducing cost is to use even lower voltage power sources. Unfortunately, as the power source voltage decreases, the drug delivery rate also decreases. Thus, there has been a need for a method of improving the performance characteristics, such as the amount of drug delivered per unit of power, of iontophoretic delivery devices to enable the use of inexpensive low-voltage power sources.

One method of increasing the rate at which drug is delivered from a transdermal iontophoretic drug delivery device is to apply the device on a skin site having optimum drug transport characteristics. For example, Abramson and Gorin in J. Phys. Chem., Vol. 44, pp 1094-1102 (1940); Burnette and Marrero, J. Pharm. Sci., Vol. 75, pp. 738-743 (1986); and Burnette and Ongpipattanakul, J. Pharm. Sci., Vol. 77, pp. 132-137 (1988) have all shown that during iontophoresis, ions are preferentially transported transdermally through shunt pathways in the skin, such as sweat ducts and hair follicles. The face and scalp have the highest density of hair follicles in humans (see Bloom and Fawcett, A Textbook of Histology, 10th ed., W.B. Saunders Co., p 594). Abramson and Gorin have further shown that iontophoretic transport takes place mainly through sweat duct skin pores rather than hair follicle skin pores. Based on this transport mechanism, one would expect that skin sites having a high density of sweat ducts and hair follicles would be preferred sites for iontophoresis. Table 1, taken from Rothman's: Physiology and Biochemistry of the Skin, Chicago, University Press, p 158 (1971), shows the distribution of sweat ducts in human skin.

TABLE 1

| Distribution of Sweat Ducts in Human Skin | |
|---|---|
| | No. per cm$^2$ |
| Palms | 424 |
| Soles | 417 |
| Dorsa of Hands | 231 |
| Forehead | 195 |
| Chest and Abdomen | 176 |
| Forearm | |
| Flexor aspect | 174 |
| Extensor aspect | 169 |
| Dorsa of Feet | 143 |
| Thigh and Leg | |
| Medical aspect | 89 |
| Lateral aspect | 86 |
| Cheek | 85 |
| Nape of Neck | 65 |
| Back and Buttocks | 65 |

Based on this data and on the known mechanism for iontophoretic drug delivery one would expect that the preferred delivery sites would be the head, hands and feet. Surprisingly, the present invention provides a method for increasing the rate at which a drug or other beneficial agent is delivered through intact human skin by selecting a skin site other than that having the highest density of sweat ducts.

DISCLOSURE OF THE INVENTION

The present invention provides a method of enhancing the rate at which an agent (e.g., a drug) is iontophoretically delivered, and to an improved method of using known iontophoretic delivery devices, by means of the intentional selection of a skin site for the transdermal delivery of the agent by iontophoresis. Use of this invention greatly increases the efficiency and efficacy of known iontophoretic drug delivery devices.

The present invention provides a method of transdermally administering a beneficial agent from an iontophoretic delivery device to a human patient. According to the present invention, the rate at which the beneficial agent is delivered through the skin of the patient may be increased by selecting a site on intact back skin of the patient and securing the donor electrode of an iontophoretic delivery device in agent-delivering relation to the selected skin site.

Any known iontophoretic delivery device may be used in accordance with the present invention. Iontophoretic delivery devices include a donor electrode assembly which includes a donor electrode and a reservoir containing the beneficial agent to be iontophoretically delivered. The donor electrode assembly is adapted to be placed in agent transmitting relation to the skin or mucosa of the patient. The device also includes a counter electrode assembly adapted to be placed in electrical contact with the skin at a location spaced apart from the donor electrode. Further, the device includes an electric power source. The electrodes and the power source are electrically connected and form a closed circuit when the electrode assemblies are placed in current conducting relation to the skin of the patient.

MODES FOR CARRYING OUT THE INVENTION

When selecting an optimum skin site for the transdermal iontophoretic delivery of a drug, a number of factors are taken into consideration. First, the rate at which drug is transported through the skin should be high enough to provide therapeutically effective plasma levels of drug at the electrical current level chosen for the particular delivery system. Secondly, the electrical resistance of the skin is preferably as low as possible. Thirdly, the variability between individual patients, in both the flux rate and the skin resistance, is preferably as low as possible. Fourthly, the skin site will preferably have a high tolerance to sensing the electrical current being applied by the device. Fifthly, the selected skin site should have as high a resistance to skin irritation as possible. The sources of potential skin irritation include (1) adverse reaction to the drug being delivered, (2) the occlusion of the skin site by the delivery device and (3) the application of electric current by the device.

Figure 1:
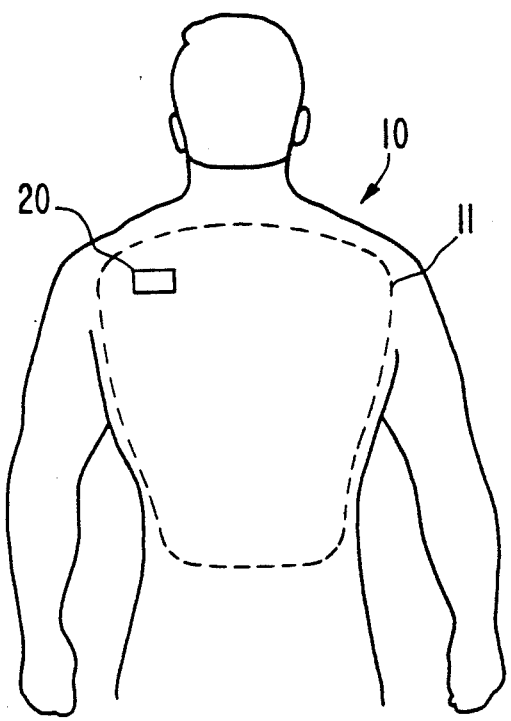
FIG. 1 is a perspective view showing the site of iontophoretic delivery according to the present invention.

Taking into consideration these five factors, it has surprisingly been discovered that human back skin is an optimum site for iontophoretic drug delivery in humans. Human back skin is best defined with reference to FIG. 1 showing a rear view of a human patient 10. Back skin is defined herein as that skin within the dotted lines 11. FIG. 1 illustrates one possible placement of an iontophoretic drug delivery device 20 on intact back skin of human patient 10.

The methods of the present invention can be used to improve the performance characteristics, such as the amount of drug delivered per unit of power, of any known iontophoretic delivery device including those described in U.S. Pat. Nos. 4,325,367; 4,474,570; 4,557,723; 4,640,689; and 4,708,716; all of which are incorporated herein by reference. Similarly, the methods of the present invention can be used to advantage with any known iontophoretic donor electrode assembly which is adapted to be connected to an external power source, including those electrode assemblies described in U.S. Pat. Nos. 4,274,420; 4,391,278; 4,419,092; and 4,702,732; all of which are incorporated herein by reference.

Figure 2:
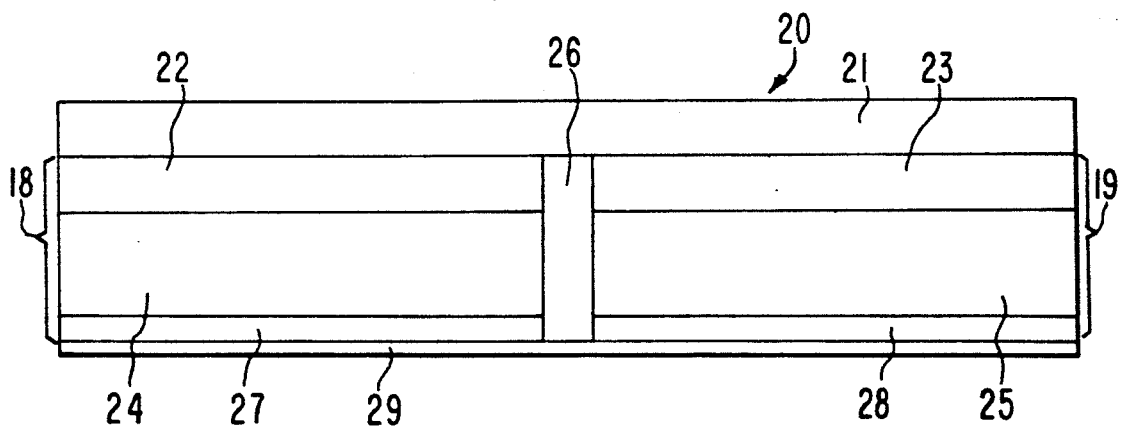
FIG. 2 is a schematic view of an iontophoretic delivery device.

FIG. 2 illustrates one example of a preferred iontophoretic delivery device 20. Device 20 has a top layer 21 which contains an electrical power supply (e.g., a battery or a series of batteries) as well as optional control circuitry such as a current controller (e.g., a resistor or a transistor-based current control circuit), an on/off switch, and/or a microprocessor adapted to control the current output of the power source over time.

Device 20 also includes electrode assembly 18 and electrode assembly 19. Electrode assemblies 18 and 19 are separated from one another by an electrical insulator 26, and form therewith a single self-contained unit. For purposes of illustration, the electrode assembly 18 will be referred to as the "donor" electrode assembly while electrode assembly 19 will be referred to as the "counter" electrode assembly. In this embodiment, the donor electrode 22 is positioned adjacent drug reservoir 24 while the counter electrode 23 is positioned adjacent the return reservoir 25 which contains an electrolyte. Electrodes 22 and 23 are formed from metal foils (e.g., silver or zinc), or a polymer matrix loaded with metal powder, powdered graphite, carbon fibers, or any other suitable electrically conductive material. Reservoirs 24 and 25 can be polymeric matrices or gel matrices. Insulator 26 is composed of a non-electrical conducting and non-ion-conducting material which acts as a barrier to prevent short-circuiting of the device 20. Insulator 26 can be an air gap, a non-ion-conducting polymer or adhesive or other suitable barrier to ion flow. The device 20 is adhered to the skin by means of ion-conducting adhesive layers 27 and 28. The device 20 also includes a strippable release liner 29 which is removed just prior to application to the skin.

In a typical device 20, the drug reservoir 24 contains an ionizable supply of the drug to be delivered and the counter reservoir 25 contains a suitable electrolyte. Alternatively, device 20 can contain an ionizable supply of drug in both reservoirs 24 and 25 and in that manner both electrode assemblies 18 and 19 would function as donor electrode assemblies. For example, positive drug ions could be delivered through the skin from the anode electrode assembly, while negative drug ions could be introduced from the cathode electrode assembly.

Generally, the combined skin-contacting area of electrode assemblies 18 and 19 can range from about 1 cm$^2$ to greater than 200 cm$^2$, but typically will range from about 5 to 50 cm$^2$.

In accordance with the present invention, the drug reservoir 24 of the iontophoretic delivery device 20 must be in agent transmitting relation with human back skin as defined by dotted lines 11. It is not necessary, however, that the return reservoir 25 also be in electrolyte transmitting relation with human back skin as defined by dotted lines 11, although this is greatly preferred.

The method of the present invention is particularly useful in optimizing the transdermal drug flux of iontophoretic drug delivery devices utilizing a low-voltage power source. In particular, the method of the present invention is useful in optimizing (i) the agent transdermal delivery rate and (ii) the amount of agent delivery per unit of power from devices powered by a low voltage power source (e.g., a battery, or a series of batteries, having a combined voltage in the range of about 1 to 10 volts).

As used herein, the expressions "agent" and "drug" are used interchangeably and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, polypeptides and other macromolecules, psychostimulants, sedatives and tranquilizers.

The device of the present invention can be used to deliver, in a controlled manner, the following drugs: baclofen, betamethasone, beclomethasone, buspirone, cromolyn sodium, dobutamine, doxazosin, droperidol, fentanyl, sufentanil, ketoprofen, lidocaine, metoclopramide, methotrexate, miconazole, midazolam, nicardipine, prazosin, piroxicam, scopolamine, testosterone, verapamil, tetracaine, diltiazem, indomethacin, hydrocortisone, terbutaline and encainide.

More preferably, the invention is useful in the controlled delivery of peptides, polypeptides and other macromolecules typically having a molecular weight of at least about 300 daltons, and typically a molecular weight in the range of about 300 to 40,000 daltons. Specific examples of peptides and proteins in this size range include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.,), follicle luteoids, $\alpha$ANF, growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

It is most preferable to use a water soluble salt of the drug or agent to be delivered.

In certain cases, it may be desirable to deliver the drug or agent with a skin permeation enhancer. The permeation enhancer can be selected from any of a wide variety of known materials capable of enhancing transdermal drug flux. Known permeation enhancers include surfactants, alkyl substituted sulfoxides, alkyl polyethylene glycols, lower alcohols and the permeation enhancers disclosed in U.S. Pat. Nos. 3,989,816; 4,405,616; 4,415,563; 4,424,210; and 4,722,726 which are incorporated herein by reference, for example.

Having thus generally described our invention, the following examples will further illustrate selected preferred embodiments.

EXAMPLE 1

The transdermal flux of metoclopramide HCl through samples of human cadaver back skin was measured using a polycarbonate test cell in which the skin sample to be tested is secured between a donor compartment and a receptor compartment. The donor compartment had a volume of 2 ml and was filled with an aqueous solution of 10 wt. % metoclopramide HCl. The receptor compartment also had a volume of 2 ml and was filled with Dulbecco's phosphate buffered saline (pH 7) sold by Gibco Laboratories, Grand Island, NY. The area of the skin samples available for transport was 1.26 $cm^2$. The test cell device was maintained at a temperature of 32° C. using an aluminum block heat exchanger. An anode comprising a disk of silver foil having a thickness of 0.025 mm was present in the donor compartment while a cathode comprising a sintered disk of powdered silver metal and silver chloride was present in the receptor compartment. Thus, the reduction of silver ions to silver metal occurred at the cathode, while the oxidation of silver to silver ions took place at the anode.

Human cadaver skin was used for the permeation studies. Before securing the skin samples between the donor and the receptor compartment of the test cell, the skin was first heat-stripped by immersing the skin sample in water maintained at 60° C. for 90 seconds allowing the epidermis layer to be separated from the dermis. Circular epidermis samples having a diameter of 2.22 cm were cut using a gasket cutting punch. The epidermis samples were then mounted in the permeation test cell with the stratum corneum side facing the donor compartment.

The electrodes of the test cell were then connected to a Model 363 Potentiostat/Galvanostat, made by EG&G Princeton Applied Research, Princeton, NJ, which supplied a constant level of direct current of 126 $\mu A$ or 100 $\mu A/cm^2$.

The test cell was in operation for four hours with each skin sample. During operation, metoclopramide was iontophoretically delivered from the donor solution through the cadaver skin into the receptor solution. The receptor solution was sampled once every hour over the four hour period. The entire volume (2 ml) of receptor solution was collected and replaced with fresh solution at each sampling point. The metoclopramide concentration in the receptor solution was determined by UV absorbance at 310 nm using a spectrophotometer manufactured by Hewlett Packard, of Palo Alto, CA, Model No. 8452A. The average metoclopramide flux for each of the four 1 hour periods was calculated and is presented in FIG. 4. Each flux data point shown in FIG. 4 was an average value from three skin specimens, all three specimens having been taken from the same cadaver.

The voltage for each skin sample was monitored throughout the experiment. A representative voltage was measured at 3.75 hours after start of operation for each skin sample and is recorded in Table 2. The power was calculated by multiplying the measured voltage at 3.75 hours by the applied current (i.e., 100 $\mu A/cm^2$). An average of the metoclopramide flux for hours three and four was calculated and is presented in Table 2. The ratio, as well as the average ratio, of average flux-to-power was then calculated and is presented in Table 2. From Table 2 it can be seen that back skin gave the highest average ratio of average flux-to-power, followed by the abdomen and upper arm.

TABLE 2

| Skin Site | Voltage* (Volts) | Power** (milliwatts) | Average Flux*** ($\mu g/cm^2 \cdot hr$) | Ratio of Average Flux-to-Power ($\mu g/cm^2 \cdot hr \cdot milliwatt$) | Average Ratio of Average Flux-to-Power ($\mu g/cm^2 \cdot hr \cdot milliwatt$) |
|---|---|---|---|---|---|
| Back | 1.37 | 0.17 | 122.2 | 708 | 431 |
|  | 2.01 | 0.25 | 76.7 | 303 |  |
|  | 1.34 | 0.17 | 93.2 | 552 |  |
|  | 1.92 | 0.24 | 67.7 | 280 |  |
|  | 1.52 | 0.19 | 65.7 | 343 |  |
|  | 2.05 | 0.26 | 103.7 | 401 |  |
| Chest | 2.54 | 0.32 | 65.7 | 205 | 204 |
|  | 2.61 | 0.33 | 64.6 | 196 |  |
|  | 2.63 | 0.33 | 69.9 | 211 |  |
| Abdomen | 1.20 | 0.15 | 58.0 | 384 | 336 |
|  | 1.49 | 0.19 | 65.1 | 347 |  |
|  | 1.72 | 0.22 | 60.0 | 277 |  |
| Hip/Thigh | 2.46 | 0.31 | 50.7 | 164 | 222 |
|  | 2.12 | 0.27 | 81.4 | 305 |  |
|  | 2.36 | 0.30 | 58.7 | 197 |  |
| Upper Arm | 1.29 | 0.16 | 66.9 | 412 | 307 |
|  | 2.83 | 0.36 | 71.8 | 201 |  |
| Forearm | 1.56 | 0.20 | 69.2 | 352 | 230 |
|  | 3.03 | 0.38 | 58.9 | 154 |  |
|  | 2.55 | 0.32 | 59.2 | 184 |  |

*Measured voltage at 3.75 hours after start of operating.
**Power = voltage (at 3.75 hours) × current (= 100 $\mu A/cm^2$).
***Average of the fluxes measured at 3 hours and 4 hours after start of operation.

COMPARATIVE EXAMPLE 1

Figure 4:
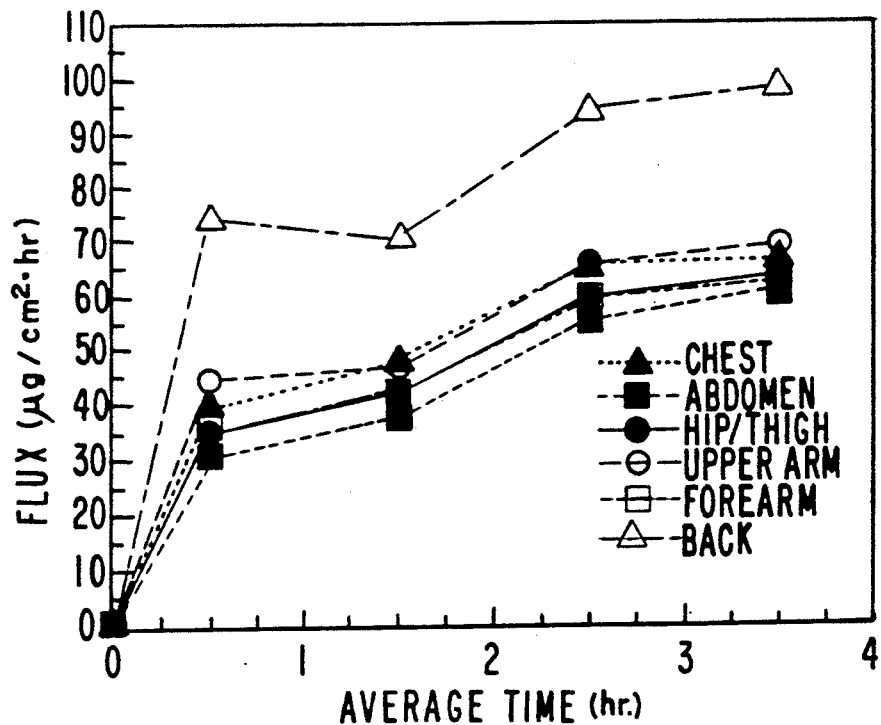
FIG. 4 is a graph showing the flux of the drug metoclopramide through human cadaver skin taken from various sites on the body of the same subject.

The same equipment and procedures described in Example 1 were used to test human cadaver skin taken from the following sites of the same cadaver tested in Example 1: abdomen, upper arm, forearm, chest and hip/thigh. The average flux of metoclopramide through these skin sites is also plotted in FIG. 4. FIG. 4 illustrates that there was a significantly higher flux of metoclopramide through human back skin than through the other tested human skin sites, i.e., the chest, abdomen, hip/thigh, upper arm and forearm. In general, the flux of metoclopramide through back skin was about 50% to 150% higher than the metoclopramide flux through the other tested skin sites.

EXAMPLE 2

The electrical resistance of human skin to direct current was tested in vivo using an iontophoretic delivery device. The device included an anode electrode assembly and a cathode electrode assembly which were secured on the skin of a subject. Both electrode assemblies were connected by wires to an electric current generator-controller which generated a constant level of direct current. Each electrode assembly comprised a silicone ring having an inner annulus filled with Dulbecco's phosphate buffer saline (pH 7) gelled with 3% hydroxyethylcellulose. The skin contacting area of the gel was 1.26 cm$^2$. The electrode assembly also included a metallic electrode soldered to the connecting wire. The anode was composed of silver while the cathode was composed of Ag/AgCl. The electrode assemblies were secured to the patient's skin using a pharmaceutically acceptable contact adhesive. The generator-controller produced a constant direct current level of 126 $\mu$A or 100 $\mu$A/cm$^2$. The devices were applied to 12 human adult subjects, six male and six female. The devices were applied to the back of each subject. Six of the twelve subjects had the devices applied to the upper back while the remaining six subjects had the devices applied to the lower back. The devices were each applied for 15 minutes and the voltage was measured at 0, 5, 10 and 15 minutes after application. The skin resistance $R_{dc}$ (kohm·cm$^2$) was then calculated using Ohm's law and by assuming that the resistance of the device was very much less than the skin resistance.

Figure 3:
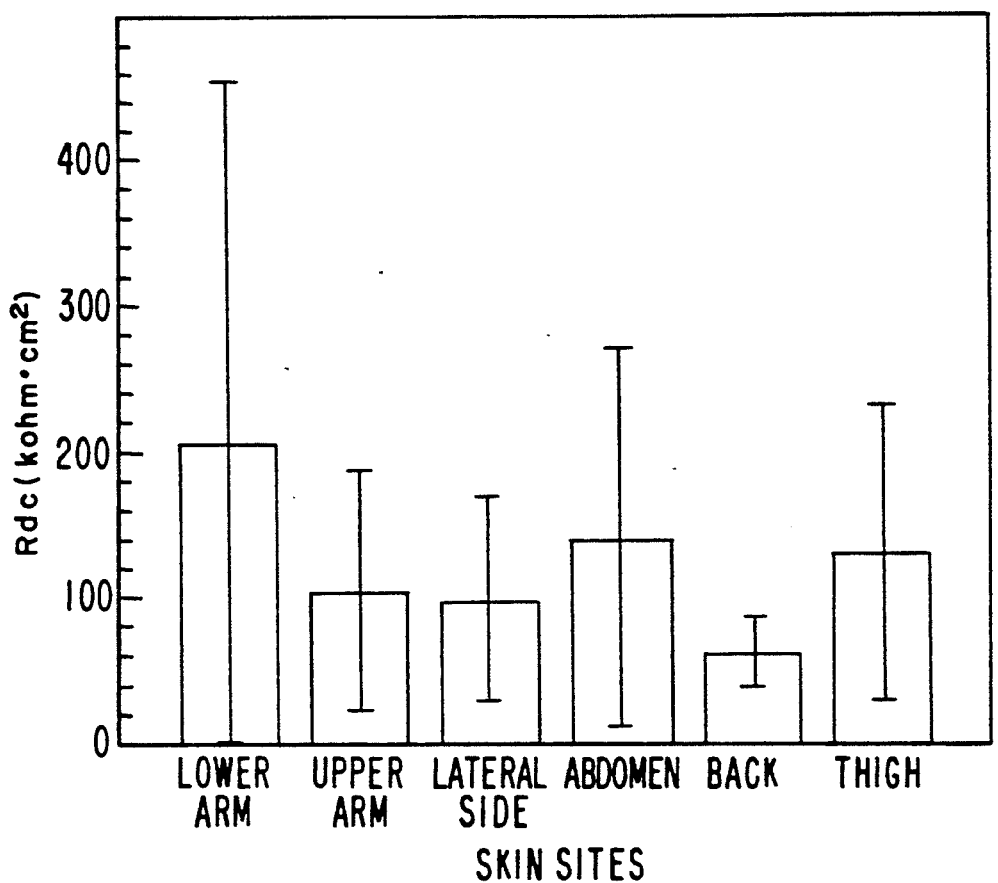
FIG. 3 is a bar graph showing the average in vivo electrical resistance of human skin taken from various subjects as well as the variability between the subjects.

Both the average back skin resistance and the standard deviation (i.e., variability) of the measurements is shown in FIG. 3.

COMPARATIVE EXAMPLE 2

The same procedures and apparatus described in Example 2 were used to test the same 12 human adult subjects, six male and six female, at different skin sites including the lower arm, the upper arm, the lateral side, the abdomen and the thigh. Both the average electrical resistance and the standard deviation of the measured resistance values (i.e., variability) is shown in FIG. 3.

A comparison of the data plotted in FIG. 3 shows that the average electrical resistance of human back skin is at least about lower than the electrical resistance of the next best skin site evaluated (e.g., the lateral side site). In addition, the variability in the electrical resistance of back skin is substantially less than the variability in the measurements of electrical resistance at the other tested skin sites.

EXAMPLE 3

The same 12 human subjects tested in Example 2 and Comparative Example 2 were monitored for skin irritation and tolerance to sensing the electric current at each of the skin sites tested. At the end of each current application, the subjects were asked to grade skin sensation as follows:

0 = no sensation
1 = detectable and acceptable sensation
2 = uncomfortable, but not unacceptable sensation
3 = unacceptable sensation Skin reactions at each of the tested skin sites were graded one hour, and again at 24 hours, following electrode removal. The skin reactions were evaluated according to the following scale.

Erythema
0 = None
1 = Barely perceptible redness
2 = Definite redness
3 = Beet redness
Extent of Erythema
0 = None
1 = Less than 50% of occluded area
2 = More than 50% of occluded area
3 = Less than 0.5 cm beyond occluded area
4 = More than 0.5 cm beyond occluded area It was found that when the delivery devices were applied to the back skin, there was negligible irritation (i.e., the average values for both erythema and extent of erythema were very much less than 1.0) of the back skin sites tested and the back skin sites exhibited no greater skin irritation than the other tested sites. Furthermore, the average sensation scores for each of the skin sites tested is presented below:

| Skin Site | Average Sensation Score |
| --- | --- |
| Upper back | 0.50 |
| Upper side | 0.83 |
| Lateral chest | 0.67 |
| Abdomen | 0.42 |
| Forearm | 0.75 |
| Upper arm | 0.50 |

Thus, the subjective evaluation of the 12 human subjects was that the back skin sites provided a clearly acceptable level, and one of the lowest levels, of sensation to the passage of a constant level (i.e., 100 $\mu$A/cm$^2$) of electrical current.

The preceding examples illustrate preferred embodiments of the present invention and are not to be construed as limiting. The scope of the invention is defined and limited only by the appended claims.

We claim:

1. A method of optimizing the transdermal flux of a beneficial agent from an iontophoretic agent delivery device through intact human skin and decreasing interpatient skin resistance variability, comprising:
   selecting a skin site on intact back skin of the human;
   placing the iontophoretic delivery device in agent transmitting relation with the intact back skin site, the delivery device contacting the back skin site over an area of about 1 to 200 cm$^2$; and
   iontophoretically delivering the agent through the back skin at a pharmaceutically effective rate, at an optimized transdermal flux compared to human skin sites other than back skin and at a transdermal flux which exhibits decreased inter-patient skin resistance variability compared to human skin sites other than back skin.

2. The method of claim 1, wherein the device includes a donor electrode assembly containing the beneficial agent and a return electrode assembly containing an electrolyte, and the method of placing the delivery device in agent transmitting relation with the back skin site includes (i) placing the donor electrode assembly in agent transmitting relation with the intact back skin site and (ii) placing the return electrode assembly in electrolyte transmitting relation with a skin site spaced apart from the selected intact back skin site.

3. The method of claim 2, wherein the method of placing the delivery device includes adhering the donor electrode assembly to the back skin site using an ion-conducting adhesive.

4. The method of claim 1, wherein the method of placing the delivery device in agent transmitting relation with the back skin site includes placing a donor electrode assembly containing the beneficial agent on the intact back skin site, placing a return electrode assembly on a skin site spaced apart from the intact back skin site and electrically connecting an electrical power source to the donor and return electrode assemblies.

5. The method of claim 4, including placing the donor electrode assembly in agent transmitting relation with a first intact back skin site and placing the return electrode assembly in electrolyte transmitting relation with a second intact back skin site, he second back skin site being spaced apart from the first back skin site.

6. The method of claim 4, including fixing the voltage of the power source.

7. The method of claim 6, wherein the voltage is fixed in the range of about 1 to 10 volts.

8. The method of claim 1, wherein the beneficial agent is a drug.

9. The method of claim 1, wherein the beneficial agent is selected from the group consisting of peptides, polypeptides, proteins and macromolecules having a molecular weight of a least about 300 daltons.

10. The method of claim 1, wherein the beneficial agent is selected from the group consisting of insulin, growth hormones, buserelin, leuprolide, LHRH, metoclopramide, fentanyl, lidocaine, ketoprofen, sufentanil, terbutaline, droperidol, heparin, interferon, scopolamine, testosterone, gonadorelin, ciclopirox olamine, buspirone, calcitonin, cromolyn sodium, and midazolam.

11. A method of optimizing transdermal flux of a beneficial agent from an iontophoretic delivery device to a human patient, comprising:
  (a) selecting a skin site on intact back skin of the human patient,
  (b) placing a donor electrode assembly, which assembly contains a beneficial agent, in agent transmitting relation with the selected intact back skin site, the donor electrode assembly contacting the back skin site over an area of about 0.5 to 100 $cm^2$,
  (c) placing a counter electrode assembly, which assembly contains an electrolyte, in electrolyte transmitting relation with a skin site spaced apart from the selected intact back skin site,
  (d) connecting an electric power source to the donor and counter electrode assemblies, and
  (e) iontophoretically delivering the agent through the back skin at a harmaceutically effective rate, at an optimized transdermal flux compared to human skin sites other than back skin, and at a transdermal flux which exhibits decreased inter-patient skin resistance compared to human skin sites other than back skin.

12. The method of claim 1 or 11, including co-delivering the beneficial agent with a skin permeation enhancer through the intact back skin.

13. The method of claim 11, wherein the power source comprises a battery having a voltage in the range of about 1 to 10 volts.

14. The method of claim 11, wherein the beneficial agent is a drug.

15. The method of claim 11, wherein the beneficial agent is selected from the group consisting of peptides, polypeptides, proteins and macromolecules having a molecular weight of at least about 300 daltons.

16. The method of claim 11, wherein the beneficial agent is selected from the group consisting of insulin, growth hormones, buserelin, leuprolide, LHRH, metoclopramide, fentanyl, lidocaine, ketoprofen, sufentanil, terbutaline, droperidol, heparin, interferon, scopolamine, testosterone, gonadorelin, ciclopirox olamine, buspirone, calcitonin, cromolyn sodium, and midazolam.

17. The method of claim 12, wherein the skin permeation enhancer comprises a surfactant.

* * * * *